United States Patent [19]

Crowley et al.

[11] Patent Number: 4,547,214
[45] Date of Patent: Oct. 15, 1985

[54] PESTICIDALLY ACTIVE AZOLYL-HYDROXY ALKANONES

[75] Inventors: Patrick J. Crowley, Crowthorne; John C. Williams, Bracknell, both of England

[73] Assignee: Imperial Chemical Industries PLC, Hertfordshire, England

[21] Appl. No.: 451,762

[22] Filed: Dec. 21, 1982

[30] Foreign Application Priority Data

Feb. 2, 1982 [GB] United Kingdom ............... 8202976

[51] Int. Cl.⁴ .................. A01N 43/50; A01N 43/64; C07D 233/60; C07D 249/08
[52] U.S. Cl. .......................... 71/76; 71/77; 71/92; 514/184; 514/383; 514/399; 548/101; 548/262; 548/341
[58] Field of Search ................. 548/101, 262, 341; 424/245, 269, 273 R; 71/76, 92

[56] References Cited

U.S. PATENT DOCUMENTS

| | | | |
|---|---|---|---|
| 4,079,143 | 3/1978 | Balasubramanyan et al. | 548/262 |
| 4,217,129 | 8/1980 | Shephard et al. | 424/245 |
| 4,394,151 | 7/1983 | de Fraine | 548/269 |

FOREIGN PATENT DOCUMENTS

2246548  5/1975  France ...................... 548/341

*Primary Examiner*—Alton D. Rollins
*Attorney, Agent, or Firm*—Cushman, Darby & Cushman

[57] ABSTRACT

Azole compounds having the general formula (I):

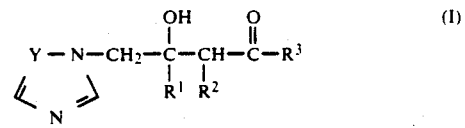

wherein Y is —CH= or =N—, $R^1$ is alkyl, cycloalkyl or optionally substituted phenyl and $R^2$ and $R^3$, which may be the same or different, are hydrogen, alkyl, cycloalkyl, (e.g. cyclopropyl, cyclopentyl or cyclohexyl), optionally substituted phenyl or optionally substituted benzyl, or together form an alkylene bridging group; and acid addition salts, metal complexes, ester and ether derivatives of the hydroxy group and stereoisomers thereof. The compounds are useful as plant fungicides and for plant growth regulation.

5 Claims, No Drawings

PESTICIDALLY ACTIVE AZOLYL-HYDROXY ALKANONES

This invention relates to triazole compounds useful as fungicides, to a process for preparing them, to fungicidal compositions containing them, and to a method of combating fungal infections in plants using them.

The triazole compounds have the general formula (I):

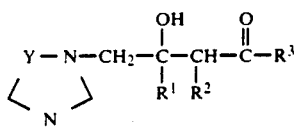

wherein Y is —CH= or =N—, $R^1$ is alkyl, cycloalkyl or optionally substituted phenyl and $R^2$ and $R^3$, which may be the same or different, are hydrogen, alkyl, cycloalkyl, (eg. cyclopropyl, cyclopentyl or cyclohexyl), optionally substituted phenyl or optionally substituted benzyl, or together form an alkylene bridging group; and the invention includes acid addition salts; metal complexes, ester and ether derivatives of the hydroxy group, and stereoisomers thereof.

The compounds of the invention can contain chiral centres. Such compounds are generally obtained in the form of racemic mixtures. However, these and other mixtures can be separated into the individual isomers by methods known in the art.

The alkyl groups can be a straight or branched chain group having 1 to 6, eg. 1 to 4, carbon atoms; examples are methyl, ethyl, propyl (n- or iso-propyl) and butyl (n-, sec-, iso- or t-butyl).

Examples of suitable substituents for the phenyl and for the phenyl moiety of the benzyl are halogen, alkyl, alkoxy, nitro and phenyl. The alkyl moiety (i.e. the α-carbon) of the benzyl can be substituted with for example one alkyl (eg. methyl or ethyl). Suitably the phenyl and benzyl are unsubstituted or substituted with 1, 2 or 3 ring substituents as defined above. Examples of these groups are phenyl, benzyl, α-methylbenzyl, 2-, 3- or 4-chloro-phenyl, 2,4- or 2,6-dichlorophenyl, 2-, 3- or 4-fluoro-phenyl, 2-, 3- or 4-bromophenyl, 2-, 3- or 4-methoxyphenyl, 2,4-dimethoxyphenyl, 2-, 3- or 4-ethoxyphenyl, 2-, 3- or 4-nitrophenyl, 2-, 3- or 4-methylphenyl, 2-, 3- or 4-trifluoromethylphenyl, 2-chloro-4-methylphenyl, 2-chloro-4-methoxyphenyl, 2-chloro-4-cyano-phenyl and 4-phenylphenyl (4-biphenylyl), and the corresponding ring substituted benzyl and α-methylbenzyl groups.

In a further aspect, therefore, the invention provides a compound of formula (I) above, or a stereoisomer thereof, wherein $R^1$ is a straight or branched chain alkyl group having from 1 to 6 carbon atoms or is phenyl optionally substituted with halogen, alkyl, alkoxy, nitro, phenyl or phenoxy; $R^2$ and $R^3$ are together an alkylene bridging group, or each represents hydrogen, straight or branched chain alkyl groups having from 1 to 6 carbon atoms, phenyl or benzyl each optionally substituted with halogen, alkyl, alkoxy, nitro, phenyl or phenoxy, the alkyl moiety (i.e. the α-carbon) of the benzyl being optionally substituted with alkyl; and Y is =CH— or =N—.

In a preferred aspect the invention provides a compound of formula (I) above, or a stereoisomer thereof, wherein $R^1$ is an alkyl group containing from 1 to 4 carbon atoms or is halophenyl, $R^2$ is hydrogen or methyl; $R^3$ is hydrogen or an alkyl group containing from 1 to 4 carbon atoms and Y is =N— or =CH—.

The salts can be salts with inorganic or organic acids eg. hydrochloric, nitric, sulphuric, acetic, 4-toluenesulphonic or oxalic acid. The ester and ether derivatives of the hydroxy group are suitably alkanoates (eg. acetates) and alkyl (eg. methyl or ethyl), aryl (eg. phenyl) or aralkyl (eg. benzyl) groups.

Suitably the metal complex is one including, as the metal, copper, zinc, manganese or iron. It preferably has the general formula:

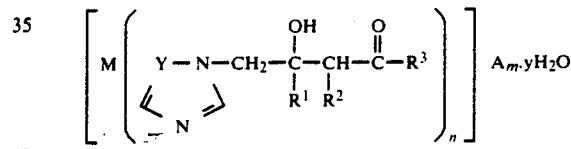

wherein Y, $R^1$, $R^2$ and $R^3$ are as defined above, M is a metal, A is an anion (eg. a chloride, bromide, iodide, nitrate, sulphate or phosphate anion), n is 2 or 4, y is 0 or an integer of 1 to 12, and m is an integer consistent with valency.

Examples of the compounds of the invention are shown in Table 1. These conform to formula I.

TABLE 1

| COMPOUND NO | $R^1$ | $R^2$ | $R^3$ | Y | MELTING POINT (°C.) |
|---|---|---|---|---|---|
| 1 | 2,4-dichlorophenyl | H | 4-phenylphenyl | =N— | 54–57 |
| 2 | 2,4-dichlorophenyl | $CH_3$ | isopropyl | =N— | 103–104 (isomer A) |
| 3 | 2,4-dichlorophenyl | $CH_3$ | isopropyl | =N— | Oil (isomer B) |
| 4 | 2,4-dichlorophenyl | *—$CH_2$—$CH_2$—$CH_2$—$CH_2$— | | =N— | 77–80 |
| 5 | 2,4-dichlorophenyl | *—$CH_2$—$CH_2$—$CH_2$— | | =N— | 157–159 |
| 6 | 2,4-dichlorophenyl | H | isopropyl | =N— | 98–100 |
| 7 | 2,4-dichlorophenyl | H | tertiary butyl | =N— | Oil |
| 8 | 2,4-dichlorophenyl | H | ethyl | =N— | Oil |
| 9 | 2,4-dichlorophenyl | $CH_3$ | n-propyl | =N— | Oil (isomer A) |
| 10 | 2,4-dichlorophenyl | $CH_3$ | n-propyl | =N— | Oil (isomer B) |
| 11 | 2,4-dichlorophenyl | H | n-propyl | =N— | Oil |
| 12 | 2,4-dichlorophenyl | $CH_3$ | ethyl | =N— | 113–114 (isomer A) |
| 13 | 2,4-dichlorophenyl | $CH_3$ | ethyl | =N— | 84–87 (isomer B) |
| 14 | 2,4-dichlorophenyl | H | phenyl | =N— | Oily Glass |

TABLE 1-continued

| COMPOUND NO | R¹ | R² | R³ | Y | MELTING POINT (°C.) |
|---|---|---|---|---|---|
| 15 | 4-(4-chloro-phenyl)phenyl | H | tertiary butyl | =CH— | |
| 16 | 4-chlorophenyl | H | ethyl | =N— | |
| 17 | 4-chlorophenyl | H | tertiary butyl | =N— | |
| 18 | 4-fluorophenyl | H | tertiary butyl | =N— | |
| 19 | 4-chlorophenyl | *—CH₂—CH₂—CH₂— | | =N— | |
| 20 | tertiary butyl | H | tertiary butyl | =N— | |
| 21 | 2,4-dichlorophenyl | H | tertiary butyl | =CH— | |
| 22 | 2,4-dichlorophenyl | H | normal butyl | =N— | |
| 23 | 2,4-dichlorophenyl | H | phenyl | =CH— | |
| 24 | 2,4-dichlorophenyl | CH₃ | tertiary butyl | =CH— | |
| 25 | 4-chlorophenyl | CH₃ | tertiary butyl | =N— | |
| 26 | 4-chlorophenyl | CH₃ | tertiary butyl | =CH— | |
| 27 | 4-(4-chloro-phenyl)phenyl | H | tertiary butyl | =N— | |

*i.e. R² and R³ together form a bridging group

The compounds of general formula (I) may be produced by reacting a compound of general formula (II) with the enolate anion (IV) generated by treatment of (III) with a strong base such as lithium diisopropylamide.

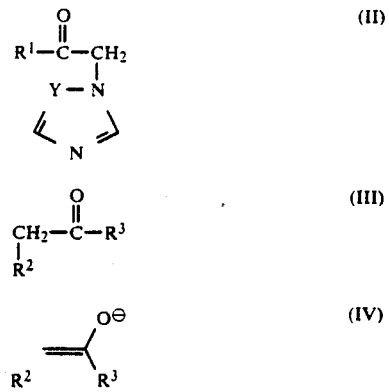

The compounds of general formula (II) and (III) may be made by methods set out in the literature.

Suitably the compounds of general formula (II) are reacted with the enolate anion (IV) in a solvent such as THF (tetrahydrofuran) at low temperature, (−78° to −40°). The product can be isolated by pouring the reaction mixture into water and recrystallising the solid formed from a convenient solvent.

The salts and metal complex of the compounds of general formula (I) can be prepared from the latter in known manner. For example, the complexes can be made by reacting the uncomplexed compound with a metal salt in a suitable solvent.

The compounds, salts and metal complexes are active fungicides, particularly against the diseases:

*Puccinia recondita, Puccinia striiformis* and other rusts on wheat, *Puccinia hordei, Puccinia striiformis* and other rusts on barley, and rusts on other hosts eg. coffee, apples, vegetables and ornamental plants.

*Erysiphe graminis* (powdery mildew) on barley and wheat and other powdery mildews on various hosts such as *Sphaerotheca fuliginea* on cucurbits (eg. cucumber), *Podosphaera leucotricha* on apples and *Uncinula necator* on vines.

*Helminthosporium* spp. and *Rhynchosporium* spp. on cereals *Cercospora arachidicola* on peanuts and other *Cercospora* species on for example sugar beet, bananas and soya beans *Botrytis cinerea* (grey mould) on tomatoes, strawberries, vines and other hosts.

*Venturia inaequalis* (scab) on apples.

Some of the compounds have also shown a broad range of activities against fungi in vitro. They have activity against various post-harvest diseases on fruit (eg. *Penicillium digatatum* and *italicum* on oranges and *Gloeosporium musarum* on bananas). Further some of the compounds are active as seed dressings against: Fusarium spp., Septoria spp., Tilletia spp. (ie. bunt, a seed borne disease of wheat), Ustilago spp., Helminthosporium spp. on cereals, *Rhizoctonia solani* on cotton and *Corticium sasakii* on rice. The compounds can move acropetally in the plant tissue. Moreover, the compounds can be volatile enough to be active in the vapour phase against fungi on the plant.

The compounds are also useful for the treatment of candidiasis and human dermatophyte infections.

The compounds also display plant growth regulating properties.

The plant growth regulating effects of the compounds are manifested as for example a stunting or dwarfing effect on the vegetative growth of woody and herbaceous mono- and di-cotyledonous plants. Such stunting or dwarfing may be useful, for example, in peanuts, cereals such as wheat and barley, oil seed rape, field beans, sunflowers, potatoes and soya bean where reduction in stem height, with or without further advantageous effects such as stem strengthening, thickening and shortening, internode shortening, increased buttress root formation and more erect stem and leaf orientation, may reduce the risk of lodging and may also permit increased amounts of fertiliser to be applied. The stunting of woody species is useful in controlling the growth of undergrowth under power lines etc. Compounds which induce stunting or dwarfing may also be useful in modifying the stem growth of sugar cane thereby increasing the concentration of sugar in the cane at harvest; in sugar cane, the flowering and ripening may be controllable by applying the compounds. Stunting of peanuts can assist in harvesting. Growth retardation of grasses can help maintenance of grass swards. Examples of suitable grasses are *Stenotaphrum secundatum* (St. Augustine grass), *Cynosurus cristatus, Lolium multiflorum* and *perenne, Agrostis tenuis, Cynodon dactylon* (Bermuda grass), *Dactylis glomerata,* Festuca spp. (eg. *Festuca rubra*) and Poa spp. (eg. *Poa pratense*). The compounds may stunt grasses without significant phytotoxic effects and without deleteriously affecting the appearance (particularly the colour) of the grass; this makes such compounds attractive for use on ornamental lawns and on grass verges. They may also have an effect on flower head emergence in for example grasses. The compounds can also stunt weed species present in the grasses; examples of such weed species are sedges (eg. Cyperus spp.) and dicotyledonous weeds (eg. daisy, plantain, knotweed, speedwell, thistle, docks and ragwort). The growth of non-crop vegetation (eg. weeds or cover vegetation) can be retarded thus assisting in the maintenance of plantation and field crops. In fruit orchards, particularly orchards subject to soil erosion, the presence of grass cover is important. However excessive grass growth requires substantial maintenance. The compounds of the invention could be useful in this situation as they could restrict growth without killing the plants which would lead to soil erosion; at the same time the degree of competition for nutrients and water by the grass would be reduced and this could result in an increased yield of fruit. In some cases, one grass species may be stunted more than another grass species; this selectivity could be useful for example for improving the quality of a sward by preferential suppression of the growth of undesirable species.

The dwarfing may also be useful in miniaturising ornamental, household, garden and nursery plants (eg. poinsettias, chrysanthemums, carnations, tulips and daffodils).

As indicated above, the compounds can also be used to stunt woody species. This property can be used to control hedgerows or to shape or reduce the need for pruning, of fruit trees (eg. apples, pears, cherries, peaches, vines etc). Some coniferous trees are not significantly stunted by the compounds so the compounds could be useful in controlling undesirable vegetation in conifer nurseries.

The plant growth regulating effect may (as implied above) manifest itself in an increase in crop yield; or in an ability in orchards and other crops to increase fruit set, pod set and grain set.

In the potato, vine control in the field and inhibition of sprouting in the store may be possible.

Other plant growth regulating effects caused by the compounds include alteration of leaf angle and changes in leaf morphology (both of which may permit increased light interception and utilization) and promotion of tillering in monocotyledonous plants. Improved light interception is of value in all major world crops, eg. wheat, barley, rice, maize, soya, sugarbeet, potatoes, plantation crops and orchard crops. The leaf angle effect may be useful for example in altering the leaf orientation of, for example, potato crops thereby letting more light into the crops and inducing an increase in photosynthesis and tuber weight. By increasing tillering in monocotyledonous crops (eg. rice), the number of flowering shoots per unit area may be increased thereby increasing the overall grain yield of such crops. In addition better control and modification of hierarchical relationships is possible both in vegetative and reproductive stages of monocotyledonous and dicotyledenous plant growth, especially in cereals such as wheat, barley, rice and maize, whereby the number of flowering shoots per unit area may be increased and the size distribution of grains within the ear may be modified in such a way as to increase yield. In the treatment of rice plants, or rice crops the invention compounds can be applied, eg. as granules or a granular formulation, for example as slow release granules, to nursery boxes, paddy water and other like cultivation loci and media.

In grass swards, especially amenity grass, an increase in tillering could lead to a denser sward which may result in increased resilience in wear; and to increased yields and better quality of forage grass, eg. improved digestability and palatability.

The treatment of plants with the compounds can lead to the leaves developing a darker green colour. In dicotyledonous plants such as soyabean and cotton, there may be promotion of sideshooting.

The compounds may inhibit, or at least delay, the flowering of sugar beet (and thereby may increase sugar yield) or otherwise modify the flowering patterns in many other crops. They may also reduce the size of sugar beet without reducing significantly the sugar yield thereby enabling an increase in planting density to be made. Similarly in other root crops (eg. turnip, swede, mangold, parsnip, beetroot, yam and cassava) it may be possible to increase the planting density.

The compounds could be useful in restricting the vegetative growth of cotton thereby leading to an increase in cotton yield. Crop yields may also be increased by improvement of the harvest index (ie. the harvested yield as a proportion of the total dry matter produced) by altering dry matter partitioning. This applies to all the aforements root, pod cereal, tree, plantation and orchard crops.

The compounds may be useful in rendering plants resistant to stress since the compounds can delay the emergence of plants grown from seed, shorten stem height and delay flowering; these properties could be useful in preventing frost damage in countries where there is significant snow cover in the winter since then the treated plants would remain below snow cover during the cold weather. Further the compounds may cause drought or cold resistance in certain plants.

When applied as seed treatments at low rates the compounds can have a growth stimulating effect on plants.

In carrying out the plant growth regulating method of the invention, the amount of compound to be applied to regulate the growth of plants will depend upon a number of factors, for example the particular compound selected for use, and the identity of the plant species whose growth is to be regulated. However, in general an application rate of 0.1 to 15, preferably 0.1 to 5, kg per hectare is used. With the use of biodegradable polymeric slow release granules rates of 1 to 10 g per hectare are feasible; whilst electrodynamic spraying techniques may also deploy lower rates of application. However, on certain plants even application rates within these ranges may give undesired phytotoxic effects. Routine tests may be necessary to determine the best rate of application of a specific compound for any specific purpose for which it is suitable.

The compounds may be used as such for fungicidal or plant growth regulating purposes but are more conveniently formulated into compositions for such usage. The invention thus provides a fungicidal or plant growth regulating composition comprising a compound of general formula (I) as hereinbefore defined, or a salt, metal complex, ether or ester thereof; and, optionally, a carrier or diluent.

The invention also provides a method of combating fungi, which comprises applying to a plant, to seed of a plant, or to the locus of the plant or seed, a compound, or salt, metal complex, ether or ester thereof, as hereinbefore defined.

The invention also provides a method of regulating plant growth, which comprises applying to the plant, to seed of a plant, or to the locus of a plant or seed, a compound, or salt, metal complex, ether or ester thereof, as hereinbefore defined.

The compounds, salts, metal complexes, ethers and esters can be applied in a number of ways, for example they can be applied, formulated or unformulated, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour; or as slow release granules. Application can be to any part of the of the plant, bush or tree, for example to the foliage, stems, branches or roots, or to soil surrounding the roots, or to the seed before it is planted.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethyl-formamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, di-acetone alcohol, toluene, kerosene, methylnaphthalene, the xylenes, trichloroethylene, furfuryl alcohol, tetrahydrofurfuryl alcohol, and glycol ethers (eg. 2-ethoxyethanol and 2-butoxyethanol).

The compositions to be used as sprays may also be in the form of aerosols wherein the formulation is held in a container under pressure in the presence of a propellant, eg. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form.

By including suitable additives, for example additives for improving the distribution, adhesive power and resistance to rain on treated surfaces, the different compositions can be better adapted for various utilities.

The compounds can be used as mixtures with fertilisers (eg. nitrogen-, potassium- or phosphorus-containing fertilisers). Compositions comprising only granules of fertiliser incorporating, for example coated with, the compound, are preferred. Such granules suitably contain up to 25% by weight of the compound. The invention therefore also provides a fertiliser composition comprising the compound of general formula (I) or a salt or metal complex thereof.

The compositions may also be in the form of liquid preparations for use as dips or sprays which are generally aqueous dispersions or emulsions containing the active ingredient in the presence of one or more surfactants eg. wetting agent(s), dispersing agent(s), emulsifying agent(s) or suspending agent(s). These agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzene-sulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10-85%, for example 25-60%, by weight of the active ingredient(s). These concentrates suitably contain organic acids (eg. alkaryl or aryl sulphonic acids such as xylenesulphonic acid or dodecylbenzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, eg. compounds having similar or complementary fungicidal activity or compounds having plant growth regulating, herbicidal or insecticidal activity.

The other fungicidal compound can be for example one which is capable of combating ear diseases of cereals (eg. wheat) such as Septoria, Gibberella and Helminthosporium spp., seed and soil borne diseases and downy and powdery mildews on grapes and powdery mildew and scab on apple etc. These mixtures of fungicides can have a broader spectrum of activity than the compound of general formula (I) alone; further the other fungicide can have a synergistic effect on the fungicidal activity of the compound of general formula (I). Examples of the other fungicidal compound are imazalil, benomyl, carbendazim, thiophanate-methyl, captafol, captan, sulphur, triforine, dodemorph, tridemorph, pyrazophos, furalaxyl, ethirimol, dimethirimol, bupirimate, chlorothalonil, vinclozolin, procymidone, iprodione, metalaxyl, forsetyl-aluminium, carboxin, oxycarboxin, fenarimol, nuarimol, fenfuram, methfuroxan, nitrotal-isopropyl, triadimefon, thiabendazole, etridiazole, triadimenol, biloxazol, dithianon, binapacryl, quinomethionate, guazitine, dodine, fentin acetate, fentin hydroxide, dinocap, folpet, dichlofluanid, ditalimphos, kitazin, cycloheximide, dichlobutrazol, a dithiocarbamate, a copper compound, a mercury compound, 1-(2-cyano-2-methoxyiminoacetyl)-3-ethyl urea, fenapanil, ofurace, propiconazole, etaconazole and fenpropemorph.

The compounds of general formula (I) can be mixed with soil, peat or other rooting media for the protection of plants against seed-borne, soil-borne or foliar fungal fungal diseases.

Suitable insecticides are piromor, croneton, dimethoate, metasystox and formothion.

Suitable insecticides are Pirimor, Croneton, dimethoate, Metasystox and formothion.

The other plant growth regulating compound can be one which controls weeds or seedhead formation, improves the level or longevity of the plant growth regulating activity of the compounds of general formula (I), selectively controls the growth of the less desirable plants (eg. grasses) or causes the compound of general formula (I) to act faster or slower as a plant growth regulating agent. Some of these other agents will be herbicides.

Examples of suitable plant growth regulating compounds, which can display synergy in admixture, or use, with the invention compounds are the gibberellins (eg. GA$_3$, GA$_4$ or GA$_7$), the auxins (eg. indoleacetic acid, indolebutyric acid, naphthoxyacetic acid or naphthylacetic acid), the cytokinins (eg. kinetin, diphenylurea, benzimidazole, benzyladenine or benzylaminopurine), phenoxyacetic acids (eg. 2,4-D or MCPA), substituted benzoic acids (eg. triiodobenzoic acid), morphactins (eg. chlorfluorecol), maleic hydrazide, glyphosate, glyphosine, long chain fatty alcohols and acids, dikegulac, fluoridamid, mefluidide, substituted quaternary ammonium and phosphonium compounds (eg. chlormequat* chlorphonium or mepiquatchloride), ethephon, carbetamide, methyl-3,6-dichloroanisate, daminozide*, asulam, abscisic acid, isopyrimol, 1-(4-chlorophenyl)-4,6-dimethyl-2-oxo-1,2-dihydropyridine-3-carboxylic acid, hydroxybenzonitriles (eg. bromoxynil), difenzoquat, benzoylprop-ethyl 3,6-dichloropicolinic acid, and tecnazene. Synergy will be most likely to occur with those of the foregoing which are quaternary ammonium compounds in particular those marked with an asterisk.

The use of the compounds of general formula (I) in conjunction with gibberellins can be useful where it is desired to reduce the plant growth regulating effects of the compounds (eg. where they are to be used as fungicides). Where the compounds are being applied to the soil surrounding the plants or to the roots of the plant, the plant growth regulating effects of the compounds may possibly be reduced by using also certain types of phenoxybenzoic acids and their derivatives.

The following Examples illustrate the invention; the temperatures are given in degrees Centigrade (°C.).

EXAMPLE 1

This Example illustrates the preparation of the compound having the chemical structure:

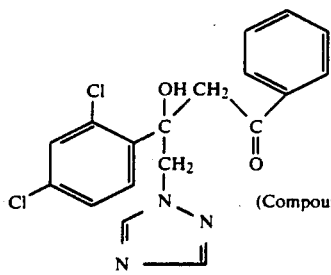

(Compound No 14 of Table 1)

n-Butyl lithium (6.5 ml of a 1.6m solution in hexane) was slowly added dropwise to diisopropylamine (1.05 g) in dry tetrahydrofuran (THF) (60 ml), stirred at −20° C. under argon. After stirring for 0.5 hr, acetophenone (1.40 g) in dry THF (10 ml) was slowly added dropwise to the solution cooled to −40° C. After stirring for 30 minutes the 2,4-dichlorophenacyltriazole (1.8 g) was slowly added in dry THF (30 ml) over 10 min, and the solution stirred at −40° for 30 minutes. The temperature was then allowed to rise to 5° over 2 hours and the reaction carefully quenched with water, and extracted with ether. The ethereal extract was dried over magnesium sulphate and then evaporated to yield an oil which was chromatographed on silica gel, eluting with ethylacetate. The product was obtained as an oily glass (0.60 g).

| | |
|---|---|
| NMR (CDCl$_3$)δ: | 3.10(d,1H), 4.64(d,1H), 4.65(d,1H), 4.98(d,1H), 5.75(s,1H), 7.14–7.94(m,8H), 7.84(s,1H), 8.20(s,1H) |
| IR (liquid film) | 3400, 1672 cm$^{-1}$ |

EXAMPLE 2

This Example illustrates the preparation of the compound

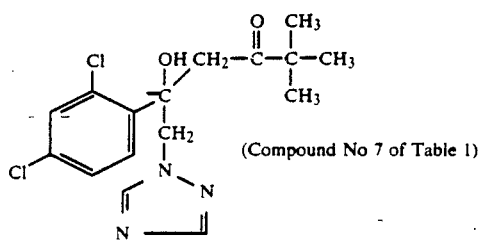

(Compound No 7 of Table 1)

n-Butyl lithium (6.5 ml of a 1.6M solution in hexane) was slowly added dropwise to diisopropylamine (1.05 g) stirred in dry tetrahydrofuran (THF) (60 ml) at −20° C. under argon. After stirring for 30 minutes, pinacolone (1.0 g) in dry THF (10 ml) was slowly added dropwise to the solution cooled to −40°, and after completion of the addition the reaction mixture was stirred at −40° for 30 minutes. 2,4-Dichlorophenacyltriazole (2.0 g) in dry THF (30 ml) was then slowly added dropwise over 10 min and the mixture stirred at −40° for 0.5 hr and then warmed to 5° over 2 hour. The reaction was then carefully quenched with water, extracted with ether and the ethereal extract dried over magnesium sulphate. Evaporation of the solvent yielded a viscous oil which was chromatographed on silica gel, eluting with ethyl acetate. The product was obtained as a viscous oil (0.60 g).

| | |
|---|---|
| NMR (CDCl$_3$)δ: | 1.00(s,9H), 2.56(d,1H), 4.10(d,1H), 4.52(d,1H), 4.92(d,1H), 5.95(s,1H), 7.14–7.40(m,2H), 7.68(d,1H), 7.78(s,1H), 8.15(s,1H) |
| IR (liquid film) | 3380, 1690 cm$^{-1}$ |

EXAMPLE 3

An emulsifiable concentrate was made up by mixing the ingredients, and stirring the mixture until all the constituents were dissolved.

| | |
|---|---|
| Compound of Example 1 | 10% |
| Ethylene dichloride | 40% |
| Calcium dodecylbenzenesulphate | 5% |
| "Lubrol" L | 10% |
| "Aromasol" H | 35% |

EXAMPLE 4

A composition in the form of grains readily dispersible in a liquid, eg. water, was prepared by grinding together the first three ingredients in the presence of added water and then mixing in the sodium acetate. The resultant mixture was dried and passed through a British Standard mesh sieve, size 44–100, to obtain the desired size of grains.

| | |
|---|---|
| Compound of Example 2 | 50% |
| "Dispersol" T | 25% |
| "Lubrol" APN5 | 1.5% |
| Sodium acetate | 23.5% |

EXAMPLE 5

The ingredients were all ground together to produce a powder formulation readily dispersible in liquids.

| | |
|---|---|
| Compound of Example 1 | 45% |
| "Dispersol" T | 5% |
| "Lissapol" NX | 0.5% |
| "Cellofas" B600 | 2% |
| Sodium acetate | 47.5% |

EXAMPLE 6

The active ingredient was dissolved in a solvent and the resultant liquid was sprayed on to the granules of China clay. The solvent was then allowed to evaporate to produce a granular composition.

| | |
|---|---|
| Compound of Example 2 | 5% |
| China clay granules | 95% |

EXAMPLE 7

A composition suitable for use as a seed dressing was prepared by mixing the three ingredients.

| | |
|---|---|
| Compound of Example 1 | 50% |
| Mineral oil | 2% |
| China clay | 48% |

EXAMPLE 8

A dusting powder was prepared by mixing the active ingredient with talc.

| | |
|---|---|
| Compound of Example 2 | 5% |
| Talc | 95% |

EXAMPLE 9

A col formulation was prepared by ball-milling the constituents set out below and then forming an aqueous suspension of the ground mixture with water.

| | |
|---|---|
| Compound of Example 1 | 40% |
| "Dispersol" T | 10% |
| "Lubrol" APN5 | 1% |
| Water | |

EXAMPLE 10

A dispersible powder formulation was made by mixing together the ingredients set out below and then grinding the mixture until all were thoroughly mixed.

| | |
|---|---|
| Compound of Example 2 | 25% |
| "Aerosol" OT/B | 2% |
| "Dispersol" A.C. | 5% |
| China clay | 28% |
| Silica | 40% |

EXAMPLE 11

This Example illustrates the preparation of a dispersible powder formulation. The ingredients were mixed and the mixture then ground in a comminution mill.

| | |
|---|---|
| Compound of Example 1 | 25% |

-continued

| | |
|---|---|
| "Perminal" BX | 1% |
| "Dispersol" T | 5% |
| Polyvinylpyrrolidone | 10% |
| Silica | 25% |
| China clay | 34% |

EXAMPLE 12

The ingredients set out below were formulated into a dispersible powder by mixing then grinding the ingredients.

| | |
|---|---|
| Compound of Example 2 | 25% |
| "Aerosol" OT/B | 2% |
| "Dispersol" A | 5% |
| China clay | 68% |

In Examples 3 to 12 the proportions of the ingredients given are by weight.

There now follows an explanation of the compositions or substances represented by the various Trade Marks and Trade Names mentioned above.

| | |
|---|---|
| LUBROL L: | a condensate of nonyl phenol (1 mole) with ethylene oxide (13 moles). |
| AROMASOL H: | a solvent mixture of alkylbenzenes. |
| DISPERSOL T & AC: | a mixture of sodium sulphate and a condensate of formaldehyde with sodium naphthalene sulphonate. |
| LUBROL APN5: | a condensate of nonyl phenol (1 mole) with naphthalene oxide (5.5 moles). |
| CELLOFAS B600: | a sodium carboxymethyl cellulose thickener. |
| LISSAPOL NX: | a condensate of nonyl phenol (1 mole) with ethylene oxide (8 moles). |
| AEROSOL OT/B: | dioctyl sodium sulphosuccinate. |
| PERMINAL BX: | a sodium alkyl naphthalene sulphonate. |

Potting Compost (No 1 or 2) in 4 cm diameter minipots. A layer of fine sand was placed at the bottom of the pots containing the dicotyledonous plants to facilitate uptake of test compounds by the roots. The test compounds were formulated either by bead milling with aqueous Dispersol T or as a solution in acetone or acetone/ethanol which was diluted to the required concentration immediately before use. For the foliar diseases, solutions and suspensions (100 ppm a.i.) were sprayed on the foliage and applied to the roots of the plant via the soil. For the test against Botrytis cinerea, grape berries were sprayed with the test compounds. The sprays were applied to maximum retention and the root drenches to a final concentration equivalent to approximately 40 ppm a.i./dry soil. Tween 20, to give a final concentration of 0.05%, was added when the sprays were applied to cereals. (a.i. means 'active ingredient')

Most were protectant tests where the compound was applied to the soil and roots and to the foliage one or two days before the plant was inoculated with the pathogen. However, in the case of the tests against Erisyphe graminis hordei and Botrytis cinerea the treatment was eradicative and the compounds were applied one day after inoculation.

Inoculation of the grape berries in the Botrytis cinerea test was achieved by slitting fruits twice and then immersing them in a spore suspension of the pathogen. The remaining foliar pathogens were applied by spray as spore suspensions onto the leaves of the test plants.

After inoculation, the plants were placed in an appropriate environment to allow infection to proceed and then incubated until the disease was ready for assessment. The period between inoculation and assessment varied from four to fourteen days according to the disease and the environment.

Disease control was recorded using the following grading system:
4=no disease
3=trace to 5% of disease on untreated plants
2=6-25% of disease on untreated plants
1=26-59% of disease on untreated plants
0=60-100% of disease on untreated plants
The results are shown in Table II.

TABLE II

| COMPOUND NUMBER | PUCCINIA RECONDITA (WHEAT) | ERYSIPHE GRAMINIS (BARLEY) | PIRICULARIA ORYZAE (RICE) | PLASMOPARA VITICOLA (VINE) | PHYTOPHTHORA INFESTANS (TOMATO) | BOTRYTIS CINEREA (GRAPE) | CERCOSPORA ARACHIDICOLA (PEANUT) | VENTURIA INEQUALIS (APPLE) |
|---|---|---|---|---|---|---|---|---|
| 1 | 4 | 4 | 3 | 1 | — | 0 | 3 | 2 |
| 2 | 4 | 4 | 4 | 0 | — | 0 | 4 | 4 |
| 3 | 4 | 4 | 3 | 1 | | 0 | 4 | 4 |
| 4 | 4 | 4 | 4 | 0 | | 0 | 3 | 4 |
| 5 | 3 | 4 | 4 | 2 | | 0 | 4 | 4 |
| 6 | 4 | 4 | 3 | 2 | | 3 | 4 | 4 |
| 7 | 4 | 4 | — | 0 | | 0 | 4 | 4 |
| 8 | 4 | 4 | 4 | 0 | | 0 | 4 | 4 |
| 9 | 4 | 4 | 3 | 0 | | 4 | 4 | 4 |
| 10 | 4 | 4 | 3 | 0 | | 0 | 4 | 4 |
| 11 | 4 | 4 | 4 | 0 | | 0 | 3 | 4 |
| 12 | 3 | 4 | 4 | 0 | | 0 | 4 | 4 |
| 13 | 3 | 4 | 4 | 1 | | 0 | 3 | 4 |
| 14 | 4 | 4 | — | 1 | | 0 | 4 | 4 |

"—" means not tested.

EXAMPLE 13

The compounds were tested against a variety of foliar fungal diseases of plants. The techniques employed were as follows. For all tests other than that against Botrytis cinerea, the plants were grown in John Innes

EXAMPLE 16

This Example illustrates the plant growth regulating properties of the compounds. The compounds were applied as an overall spray of an emulsifiable concentrate diluted to give the concentrations shown in Table III. The plants were grown in 3" pots in peat compost and sprayed at the 2 leaf stage. Plant growth regulating effects were assessed 12 days after application of the compounds. Retardation of growth was scored on a 0–3 scale where:

1 = 0–30% retardation
2 = 31–75% retardation
3 = 75% retardation

Additional plant growth regulating properties are indicated as follows:

G = darker green leaf colour
A = apical effect
T = tillering effect

The results are shown in Table III. If no figure is shown the compound was substantially inactive as a stunting agent.

TABLE III

| COMPOUND | DAT | RATE (ppm) | AT | CC | DA | LT | SB | TO | SY | CT | MZ | WW | BR |
|---|---|---|---|---|---|---|---|---|---|---|---|---|---|
| 1 | 19 | 4000 | — | — | — | 1 | 1G | 2GA | 1GT | 2A | 2A | — | — |
| 5 | 19 | 4000 | 2G | 2G | 2 | — | 2G | 2GA | 2G | 3GA | 2 | 1 | 1 |
| 6 | 19 | 4000 | 1 | 1G | — | 3G | 2G | 2GAT | 1 | 2GA | 1 | 1GT | 1 |
| 7 | 19 | 400 | 1 | 1 | 1 | 3G | 3G | 3GT | 1 | 2 | — | — | — |
| 11 | 19 | 4000 | 2G | 2G | 2G | 1 | 2G | 2GT | 2GAT | 2A | 2 | 1G | 1G |
| 12 | 19 | 4000 | 3 | 2 | 2G | 3 | 3G | 3GA | 2A | 2GA | 3GA | 2GT | 2GT |
| 14 | 19 | 4000 | 2 | 1 | 1 | 1 | 3G | 3G | 3G | — | — | — | — |

Key to test species in Table III
AT *Agrostis tenuis*
CC *Cynosurus cristatus*
DA *Dactylis glomerata*
LT *Lactuca sativa*
SB *Beta vulgaris*
TO *Lycopersicon esculentum*
SY *Glycine max*
CT *Gossypium hirsutum*
MZ *Zea mays*
WW *Triticum aestivum*
BR *Hordeum vulgare*

We claim:

1. An azole compound selected from the group consisting of compounds having the formula (I):

$$Y-N-CH_2-\underset{\underset{R^1}{|}}{\overset{\overset{OH}{|}}{C}}-\underset{\underset{R^2}{|}}{CH}-\overset{\overset{O}{\|}}{C}-R^3 \quad (I)$$

wherein Y is =N—; $R^1$ is 4-chlorophenyl or 2,4-dichlorophenyl; $R^2$ is methyl or ethyl and $R^3$ is alkyl having from 1 to 4 carbon atoms; and acid addition salts, metal complexes, lower alkanoate, lower alkyl or benzyl derivatives of the hydroxy group and stereoisomers thereof.

2. A compound according to claim 1 selected from the group of compounds represented by the following combinations of values for $R^1$, $R^2$, $R^3$ and Y:

| $R^1$ | $R^2$ | $R^3$ | Y |
|---|---|---|---|
| 2,4-dichlorophenyl | $CH_3$ | isopropyl | =N— |
| 2,4-dichlorophenyl | $CH_3$ | n-propyl | =N— |
| 2,4-dichlorophenyl | $CH_3$ | ethyl | =N— |
| 4-chlorophenyl | $CH_3$ | tertiary butyl | =N— |

3. A fungicidal, or plant growth regulating composition comprising an effective amount of a compound as claimed in claim 1, and a carrier or diluent.

4. A method of regulating the growth of plants, which comprises applying to the plant, to seed of the plant, or to the locus of the plant or seed, an effective amount of a compound as claimed in claim 1.

5. A method of combating fungal diseases in a plant, which method comprises applying to the plant, to seed of the plant or to the locus of the plant or seed, an effective amount of a compound as claimed in claim 1.

* * * * *